(12) United States Patent
Cumming

(10) Patent No.: US 10,463,475 B2
(45) Date of Patent: *Nov. 5, 2019

(54) INTRAOCULAR LENS

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 196 days.

This patent is subject to a terminal disclaimer.

(21) Appl. No.: 15/139,679

(22) Filed: Apr. 27, 2016

(65) Prior Publication Data

US 2016/0235521 A1 Aug. 18, 2016

Related U.S. Application Data

(63) Continuation of application No. 14/741,230, filed on Jun. 16, 2015, now Pat. No. 9,358,101, which is a continuation of application No. 14/035,821, filed on Sep. 24, 2013, now Pat. No. 9,295,545, and a continuation-in-part of application No. 13/910,076, filed on Jun. 4, 2013, now Pat. No. 9,295,544.

(60) Provisional application No. 61/689,394, filed on Jun. 5, 2012.

(51) Int. Cl.
*A61F 2/16* (2006.01)

(52) U.S. Cl.
CPC ............ *A61F 2/1624* (2013.01); *A61F 2/16* (2013.01); *A61F 2/1629* (2013.01); *A61F 2/1635* (2013.01); *A61F 2/1645* (2015.04); *A61F 2002/1681* (2013.01); *A61F 2002/1682* (2015.04)

(58) Field of Classification Search
CPC .... A61F 2/1613; A61F 2/1624; A61F 2/1629; A61F 2/1635; A61F 2/1637; A61F 2/1648; A61F 2002/1681; A61F 2002/1689; A61F 2002/1682

See application file for complete search history.

(56) References Cited

U.S. PATENT DOCUMENTS

| | | | |
|---|---|---|---|
| 2,834,023 A | 5/1958 | Lieb |
| 4,073,014 A | 2/1978 | Poler |
| 4,118,808 A | 10/1978 | Poler |
| 4,122,556 A | 10/1978 | Poler |
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.

(Continued)

*Primary Examiner* — William H Matthews
(74) *Attorney, Agent, or Firm* — Sheppard Mullin Richter & Hampton LLP

(57) ABSTRACT

An intraocular lens comprising a lens optic coupled to at least one haptic and at least one deformable connecting bar positioned between the lens optic and the at least one haptic. The lens is designed to provide uncorrected vision for distance, intermediate and near vision.

27 Claims, 1 Drawing Sheet

(56) References Cited

U.S. PATENT DOCUMENTS

| | | |
|---|---|---|
| 4,206,518 A | 6/1980 | Jardon et al. |
| 4,244,060 A | 1/1981 | Hoffer |
| 4,254,509 A | 3/1981 | Tennant |
| 4,257,521 A | 3/1981 | Poler |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,615,702 A | 8/1986 | Koziol |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,666,445 A | 5/1987 | Tillay |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |
| 4,731,078 A | 3/1988 | Stoy |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,767,904 A | 8/1988 | Braden et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,089,022 A | 2/1992 | Koester et al. |
| 5,139,518 A | 8/1992 | White |
| 5,141,507 A | 8/1992 | Paraekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,762,836 A | 9/1998 | Bos |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,413,277 B1 | 7/2002 | Neuhann |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |

(56) References Cited

U.S. PATENT DOCUMENTS

| | | |
|---|---|---|
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,932,839 B1 | 8/2005 | Kamerling et al. |
| 6,942,695 B1 | 9/2005 | Chapoy |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 | 7/2014 | Cumming |
| 9,034,036 B2 | 5/2015 | Cumming |
| 9,211,186 B2 | 12/2015 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0111151 A1 | 10/2004 | Paul |
| 2004/0215207 A1 | 10/2004 | Cumming |
| 2004/0215340 A1 | 10/2004 | Messner et al. |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0149184 A1 | 1/2005 | Bogaert |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0021832 A1 | 1/2007 | Nordan |
| 2007/0032867 A1 | 2/2007 | Cumming |
| 2007/0005136 A1 | 4/2007 | Richardson |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0188930 A1 | 7/2008 | Mentak |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2012/0296424 A1 | 11/2012 | Betser |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0094909 A1 | 4/2014 | Cumming |
| 2014/0155871 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |
| 2015/0182327 A1 | 7/2015 | Cumming |
| 2015/0182328 A1 | 7/2015 | Cumming |
| 2015/0245904 A1 | 9/2015 | Cumming |
| 2015/0245905 A1 | 9/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |

(56) References Cited

FOREIGN PATENT DOCUMENTS

| WO | WO 2007/037180 | 4/2007 |
|----|----------------|--------|
| WO | 2008/150890 A1 | 12/2008 |
| WO | WO 2009/048656 | 4/2009 |
| WO | WO 2009/086511 | 7/2009 |
| WO | WO 2011/151839 | 12/2011 |

OTHER PUBLICATIONS

International Search Report and Written Opinion for PCT/US13/61452 dated Feb. 24, 2014 in 11 pages.
International Search Report and Written Opinion for PCT/US2014/057037 dated Jan. 20, 2015 in 12 pages.
International Search Report and Written Opinion for PCT/US2014/072518 dated Jul. 23, 2015 in 15 pages.
Internet Archive Wayback Machine; Crystalens—Is Crystalens right for you?; downloaded from http://web.archive.org/web/20141025080709/http://crystalens.com/en-us/iscrystalensrightforyou.aspx (Archived Oct. 25, 2014; printed on Aug. 12, 2015).
Davison, J.A., Chapter 11: Intraocular Lenses, *Duane's Clinical Ophthalmology on CD-ROM*, Lippincott Willliams & Wilkins, 2005, vol. 6, pp. 1-46.

INTRAOCULAR LENS

CROSS-REFERENCE TO RELATED APPLICATIONS

This application is a continuation of U.S. patent application Ser. No. 14/741,230, filed on Jun. 16, 2015, now U.S. Pat. No. 9,358,101, which is a continuation of U.S. patent application Ser. No. 14/035,821, filed on Sep. 24, 2013, now U.S. Pat. No. 9,295,545, which is a continuation-in-part of U.S. patent application Ser. No. 13/910,076, filed on Jun. 4, 2013, now U.S. Pat. No. 9,295,544, and also claims priority to U.S. Provisional Application No. 61/689,394, filed on Jun. 5, 2012, the contents of which are hereby incorporated by reference herein in their entireties.

BACKGROUND

The present disclosure is related to a single focus intraocular lens, various embodiments of which provide seamless vision from distance to near automatically.

DESCRIPTION OF THE RELATED ART

An intraocular lens (IOL) is a lens implanted into the eye, usually replacing a normal human lens that has been clouded over by a cataract, or can replace a normal human lens as a form of refractive surgery to change the eye's optical power.

Premium intraocular lenses (IOLs) implanted during cataract surgery are categorized three ways: accommodating, multifocal, and toric intraocular lenses.

The best visual acuity is achieved with the single focus accommodating lenses. The optic of these lenses moves forward and backward upon constriction and relaxation of the ciliary muscle. However, for reading in dim lighting conditions, or for small print, weak reading glasses are often necessary.

The multifocal lenses focus light on the retina at either two or three focal lengths. Thus, there is more than one image on the retina simultaneously. This creates problems since the amount of light in focus is divided between the multiple focal points, and contrast sensitivity is thereby reduced, making vision at all distances difficult in dim lighting. In addition, there are severe problems when driving at night when the pupil is dilated. Many patients experience severe glare and halos and many have had to have the multifocal lenses explanted and replaced with a single vision standard lens, because of this problem. However, the near vision with the multifocal lenses is superior to that of the current accommodating lens.

The toric lenses correct the eyes that have significant astigmatism.

The currently marketed plate accommodating intraocular lenses provide excellent distance and intermediate vision but sometimes can require weak, +1.00, reading glasses for prolonged reading, for seeing small print, or reading in dim lighting conditions.

Furthermore, it is important for intraocular lenses to have a consistent location along the axis of the eye to provide good uncorrected distance vision and to center in the middle of the vertical meridian of the eye. Without excellent uncorrected distance vision there is no point in implanting lenses designed to give seamless vision from far to near.

The original intraocular lens consisted of a single optic. These lenses frequently de-centered and dislocated and it was discovered that there was a need to center and fixate the lens optic in the vertical meridian of the eye.

Attachments to the optic that center and fixate the lens within the capsular bag are called haptics. Traditionally, haptics comprised multiple flexible loops of various designs, J loops, C loops, closed loops, and flexible radial arms. Recently, traditional haptics have been replaced in some lens designs with oblong, flat flexible plates, called plate haptics. These plate haptics usually made from silicone, are solid, flat, flexible and between 3.0 and 6.0 mm in width, 0.20 to 0.75 mm thick, and may have tapered, rounded or parallel sides. Plate haptics often have flexible loops or fingers that help center and fixate the lens within the capsular bag. These flexible fingers extend beyond the distal or outer end of the plate haptics and slightly beyond the diameter of the capsular bag and are designed to flex centrally to center and fixate the lens and its optic within the capsular bag.

IOLs are known to include opposing haptics positioned on either side of a lens optic. Once a patient's cataract is removed, e.g. by phacoemulsification, the IOL is placed into the empty capsular bag. The haptics help to center the IOL and fixate it within the capsular bag by fibrosis. Such IOLs are described in U.S. Pat. Nos. 5,674,282, 5,476,514, and 5,496,366, to Cumming, herein incorporated by reference in its entirety.

Moreover, although current IOLs provide patients with significantly restored distance and intermediate vision, adequate near vision is commonly lacking—often requiring that patients use weak reading glasses to enhance near vision.

SUMMARY OF THE INVENTION

An intraocular lens according to an embodiment of the present disclosure is described that overcomes the deficiencies of present designs noted above.

In various embodiments, an intraocular lens comprises a lens optic coupled to at least one haptic and a torsion bar positioned between the lens optic and the at least one haptic.

The connecting portion unlike a flat hinge flexing mechanism or a flat thin stretching hinge may have a cross section that can be round, oval, square or any variation of these. The connecting portion can have a length of between about 0.1 to 1.5 mm, in various embodiments between about 0.5 and 1.0 mm, or between about 0.1 mm to 1.0 mm. The connecting portion can connect tangentially to the optic in a transverse direction across the lens body, or connect in a radial or perpendicular manner, to function by stretching, thinning, rotating, or any combination of these.

Certain aspects of this disclosure are directed toward an intraocular lens. The intraocular lens can include a lens optic having a diameter, at least one haptic coupled to the lens optic, and at least one connecting bar connecting the lens optic and the at least one haptic. The connecting bar can have a width and thickness less than 30% the diameter of the optic.

Certain aspects of this disclosure are directed toward an intraocular lens having a lens optic coupled to at least one haptic. The at least one haptic can be primarily disposed on opposite first and second sides of the lens optic. The first side, the lens optic, and the second side can be arranged along a longitudinal axis of the intraocular lens. The at least one connecting bar can connect the lens optic and the at least one haptic. The at least one connecting bar can have a length disposed substantially orthogonal to said longitudinal axis of said accommodating intraocular lens.

Certain aspects of this disclosure are directed toward an intraocular lens having a lens optic coupled to at least one haptic. The at least one haptic can be primarily disposed on opposite first and second sides of the lens optic. The first side, the lens optic, and the second side can be arranged along a longitudinal axis of the intraocular lens. The at least one connecting bar can connect the lens optic and the at least one haptic. The at least one connecting bar can have a length disposed substantially parallel to said longitudinal axis of said intraocular lens.

Certain aspects of this disclosure are directed toward an intraocular lens having a lens optic coupled to at least one haptic. The at least one haptic can be primarily disposed on opposite first and second sides of the lens optic. The first side, the lens optic, and the second side can be arranged along a longitudinal axis of the intraocular lens. The at least one connecting bar can connect the lens optic and the at least one haptic. The at least one connecting bar can have a length disposed at an angle within about 30 degrees (e.g., within about 10 degrees, about 15 degrees, within about 20 degrees, or about 25 degrees) from said longitudinal axis of said intraocular lens.

Certain aspects of this disclosure are directed toward an intraocular lens having a lens optic coupled to at least one haptic. The at least one haptic can be primarily disposed on opposite first and second sides of the lens optic. The first side, the lens optic, and the second side can be arranged along a longitudinal axis of the intraocular lens. The at least one connecting bar can connect the lens optic and the at least one haptic. The at least one connecting bar can have a length disposed at an angle within about 30 degrees (e.g., at least about 10 degrees, about 15 degrees, about 20 degrees, or about 25 degrees) from an axis orthogonal to said longitudinal axis of said intraocular lens (i.e., a transverse axis of said intraocular lens).

In any of the above mentioned aspects, the intraocular lens may further include an optic appendage attached to said lens optic. The connecting bar can connect the optic appendage and the at least one haptic. In other aspects, the connecting bar directly connects the optic to the at least one haptic.

In any of the above mentioned aspects, the connecting bar can have a length between about 0.1 and 2.0 mm.

In any of the above mentioned aspects, the connecting bar can have a circular cross-section orthogonal to the length of the bar. In other aspects, the connecting bar can have an ovular cross section orthogonal to the length of the bar. In yet other aspects, the connecting bar can have a square cross-section orthogonal to the length of the bar.

In any of the above mentioned aspects, the connecting bar can be configured to elongate. In certain aspects, the connecting bar can be configured to thin. In certain aspects, the connecting bar can be configured to rotate.

In any of the above mentioned aspects, the connecting bar can include the same material as the haptic. In other aspects, the connecting bar includes a different material than the haptic.

In any of the above mentioned aspects, the intraocular lens can include an elongate slot partially traversing the haptic in the transverse direction of said intraocular lens. In certain aspects, the slot can be between 0.1 to 0.5 mm in height and 2 to 5 mm in length.

In any of the above mentioned aspects, the intraocular lens may not include a hinging feature between the lens optic and the haptic.

Other features and advantages of the present disclosure will become apparent from the following more detailed description, taken in conjunction with the accompanying drawings, which illustrate, by way of example, the principles of the presently described apparatus and method of its use.

DETAILED DESCRIPTION OF THE PREFERRED EMBODIMENTS

The above-described drawing figures illustrate the described disclosure in at least one of its preferred embodiments, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present disclosure.

Figure 1:
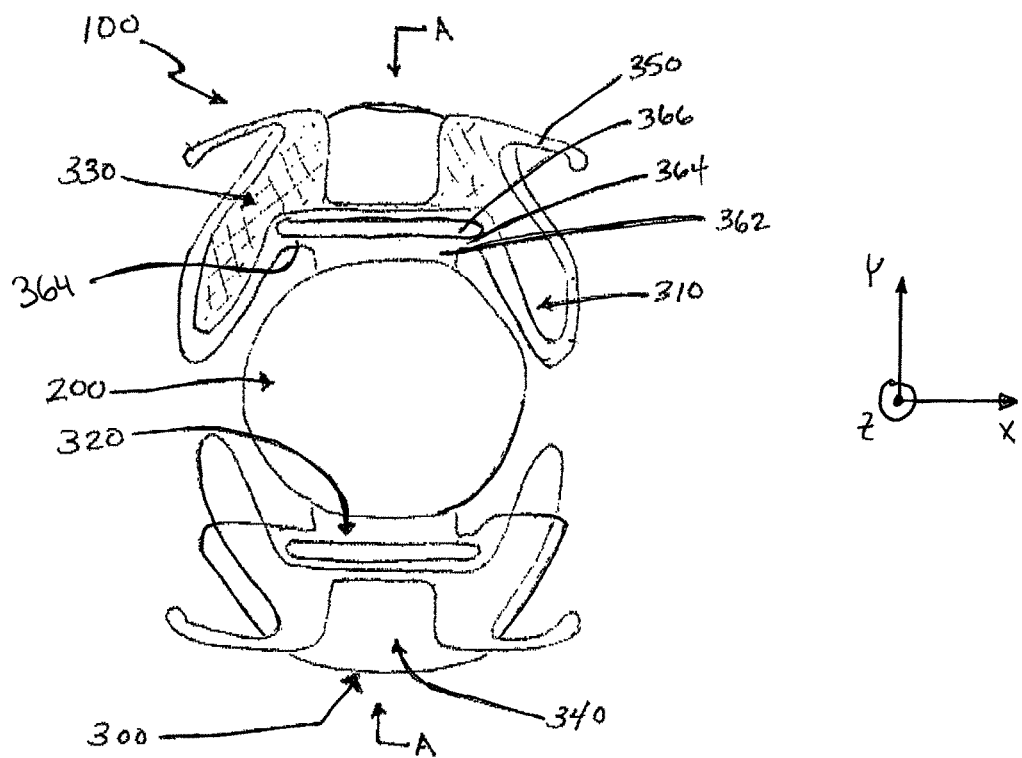
FIG. 1 illustrates a top plan view of an IOL according to at least one embodiment of the present disclosure with torsion bars connecting the optic to the haptics.

FIG. 1 illustrates intraocular lens (IOL) 100 comprising an optic 200 a short appendage 362 attached to the optic and coupled to at least one haptic 300 as well as connection bars 364 connecting the optic to the at least one haptic via the appendage 362.

The IOL 100 is placed into the capsular bag of a patient's eye during cataract surgery involving known techniques such as, for example, phacoemulsification. The lens is centered so that the optical axis of the lens coincides with that of the patient's eye. The haptics 300 contact the capsular bag and the natural fibrosis of the tissue secures the haptics 300, and consequently the IOL 100, in place.

The optic 200 is preferably a single focus optic that gathers the incoming light and focuses it on the retina of the patient to affect vision. The optic 200 may be biconvex, refractive, diffractive, plano-convex, Fresnel, spheric, aspheric, toric, or of any other type that is preferably substantially single focus. In order to permit the optic 200 to be inserted into the eye through a small incision, the optic 200 is preferably made of a flexible optical material, such as, for example, silicone, acrylic, hydrogel, or other flexible optical material now known or hereafter developed.

The at least one haptic 300 comprises a first end 320 opposite a second end 340. The first end 320 of the haptic 300 can be proximal the optic 200 while the second end is distal to the optic. The first end 320 is flexibly coupled to a periphery of the optic 200 or short appendage 362. In at least one embodiment, the IOL 100 comprises opposing haptics positioned linearly along a longitudinal axis A of the IOL 100 (e.g., parallel to the y-axis).

The haptic body may be substantially rigid in the longitudinal direction (e.g., parallel to the y-axis). While the plate haptic is substantially rigid, the flexibility of the connecting bar may promote vaulting. In various embodiments, the haptic 300 is constructed of the same or similar flexible material as the optic, including, but not limited to: silicone, hydrogel, acrylic, or similar material.

The plate haptic 300 may comprise opposing lateral paddles 310. The paddles 310 and projecting fingers 350 operable to engage, fixate, and center the AIOL in the capsular bag to locate the optic posteriorly along the axis of the eye. In certain aspects, the paddles 310 can include a different, more rigid material than the plate haptics 300. For example, the paddles 310 can be made of polyimide, prolene, or titanium. The paddles also help stabilize the lens to prevent the IOL from tilting. The paddles can also prevent anterior dislocation of one of the two plate haptics. Such exemplary haptics 300 and paddles 310 are discussed in U.S. Patent Publication No. 2011-0313519 A1, published Dec. 22, 2011 (U.S. patent application Ser. No. 13/017,189); U.S. Patent Publication No. 2011-0313524 A1, published Dec. 22, 2011 (U.S. patent application Ser. No. 13/092,359); U.S. Patent Publication No. 2011-0313525 A1, published Dec. 22, 2011 (U.S. patent application Ser. No. 13/111,599); and U.S. Patent Publication No. 2011-0313526 A1, published Dec. 22, 2011 (U.S. patent application Ser. No. 13/155,327), incorporated herein by reference in their entireties.

The paddles 310 and/or the plate haptics 300 together can surround at least a portion of the optic or surround a majority of the optic. The paddles 310 and/or the plate haptics 300 together can surround between about 100 to 350 degrees of the optic, for example, between about 100 and 200 degrees, between about 150 degrees and 250 degrees, between about 200 degrees and about 300 degrees, or between about 250 degrees and 350 degrees. The paddles 310 together extend along the sides of the optic and more particularly about 50%, 60%, 70%, 80% or more of the length of the optic. In various embodiments, the paddles 310 extend along the optic 200 in the lateral direction (parallel to the x-axis) at least about 10% the diameter of the optic. In certain aspects, the paddles can include curved edges, for example, as shown in the figures, the paddles can curve inward to at least partially conform to the shape of the optic. In certain aspects, a length of the paddle can be at least two times, at least three times, or at least four times longer than a width of the paddle. In certain aspects, an end of the paddle closest to the optic can be tapered.

A frame 330 may be embedded within the haptic 300. The frame 330 may be formed of polyimide, prolene, polymethylmethanylate (PMMA), titanium, or similar material. The frame 330 may be a meshwork or lattice, designed and shaped in a manner to make the plate haptics rigid longitudinally. Such exemplary frames 330 are discussed in U.S. Patent Publication No. 2011-0313519 A1, published Dec. 22, 2011 (U.S. patent application Ser. No. 13/017,189); U.S. Patent Publication No. 2011-0313524 A1, published Dec. 22, 2011 (U.S. patent application Ser. No. 13/092,359); U.S. Patent Publication No. 2011-0313525 A1, published Dec. 22, 2011 (U.S. patent application Ser. No. 13/111,599); and U.S. Patent Publication No. 2011-0313526 A1, published Dec. 22, 2011 (U.S. patent application Ser. No. 13/155,327), incorporated herein by reference in their entireties.

The haptic 300 may further comprise projections 350, or fingers, extending from the second end (distal to the optic 200) to engage the capsular bag and secure and center the IOL thereto. The projections 350 may be homogeneous with the frame and may be made of either polyimide, PMMA, acrylic or any other inert material. Such exemplary projections 350 are discussed in U.S. Patent Publication No. 2011-0313519 A1, published Dec. 22, 2011 (U.S. patent application Ser. No. 13/017,189); U.S. Patent Publication No. 2011-0313524 A1, published Dec. 22, 2011 (U.S. patent application Ser. No. 13/092,359); U.S. Patent Publication No. 2011-0313525 A1, published Dec. 22, 2011 (U.S. patent application Ser. No. 13/111,599); and U.S. Patent Publication 2011-0313526 A1, published Dec. 22, 2011 (U.S. patent application Ser. No. 13/155,327), incorporated herein by reference in their entireties.

The first end 320 of the haptic 300 (e.g., proximal to the optic 200) may be coupled to the optic or short appendage of the optic 362 via one or more connecting portions. The connecting portions, bars, or members, 364 shown in FIG. 1 are capable of stretching, bending, and/or potentially rotating. Depending on the configuration of the connecting portions 364, the connecting portions 364 may stretch along the length thereof, which may be at least in part along a direction substantially parallel to the longitudinal axis of the IOL and/or may be at least partly along an axis that is substantially perpendicular to the longitudinal axis of the IOL or along the transverse direction (e.g., parallel to x-axis and/or z-axis). Further, the connecting portions 364 may twist or rotate about an axis along the length of the connecting portion, which may be about an axis that is substantially perpendicular to the longitudinal axis of the IOL (e.g. about an axis parallel to z-axis and/or x-axis) and/or may be about an axis that is substantially parallel to the longitudinal axis of the IOL (e.g. about an axis parallel to y-axis) in some cases. In some embodiments, each of the connecting portions 364 can be positioned adjacent the optic periphery and flexibly coupled thereto. The connecting portions 364 can be oriented such that their length extends along an axis substantially parallel to a transverse axis of the IOL 100 (e.g. along an axis parallel to the x-axis) as shown in FIG. 1 or substantially parallel to a longitudinal axis of the IOL 100 as shown in FIG. 2.

With continued reference to FIG. 1, as disclosed above, one or more connecting portions 364 can be oriented along an axis substantially parallel to a transverse axis of the IOL 100 (e.g. parallel to the x-axis). The IOL 100 can include two connecting portions 364 for securing each haptic 300 to the short appendage 362 and optic 200. The connecting portions 364 can connect the haptic 300 to the short appendage 362 such that an elongate slot 366 is formed completely through the appendage 362 or between the short appendage 362 and the haptic 300. An elongate axis of the elongate slot 366 can be substantially perpendicular to the longitudinal axis of the IOL through line A-A (e.g. perpendicular to the y-axis) in some embodiments. Although not shown, the connecting portions 364 may be oriented along an axis that is less than or equal to about 5°, 10°, 15° 20°, 25°, 30°, 35°, 40°, or 45° from the transverse axis of the IOL (e.g., axis parallel to x-axis).

The elongate slot 366 can be an aperture formed in the haptic 300 that extends laterally and parallel to the transverse direction (e.g. parallel to the x-axis). Preferably, the slot 366 comprises an oval shape, but all shapes are specifically contemplated. As mentioned above, the slot 366 is adjacent the connecting portions distal to the optic 200. Preferably, the slot dimensions ranging from 0.1 to 0.5 mm in height and 2.0 to 5.0 mm in length.

Figure 2:
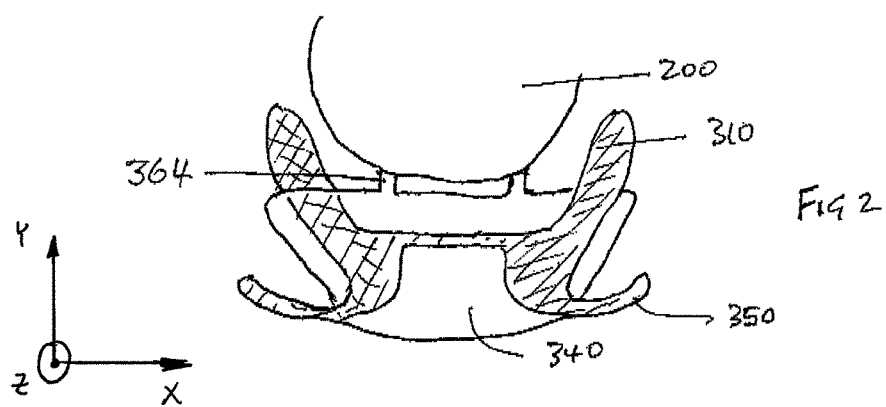
FIG. 2 illustrates a portion of an IOL according to another embodiment of the present disclosure with generally longitudinally directed connector bars connecting the optic to the haptics.

As shown in FIG. 2, one or more connecting portions or connecting bar 364 can be oriented or extend along an axis that is substantially parallel to a longitudinal axis of the AIOL 100 (e.g. along an axis parallel to the y-axis). In some embodiments, the AIOL 100 can include two connecting portions or bars 364 for securing each haptic 300 to the optic 200 although more or less are possible. For example, although not shown, each haptic 300 can be connected to the optic 200 by a single connecting portion 364. Although not shown, the connecting portions 364 may be oriented along an axis that is less than or equal to about 5°, 10°, 15° 20°, 25°, 30°, 35°, 40°, or 45° from the longitudinal axis of the IOL (e.g., axis parallel to y-axis).

The connecting portions 364 can connect the haptic 300 to the optic 200 such that an elongate slot is formed between the optic 200 and the haptic 300. An elongate axis of the elongate slot can be substantially perpendicular to the longitudinal axis of the IOL through line A-A (e.g. parallel to the x-axis).

The connecting portions 364 couples the optic 200 to the haptic 300 and is preferably of the same material as the optic. Likewise, in various embodiments, the connecting portions 364 may not include a hinge feature, for example, between the optic 200 or appendage 362 and the haptic 300 about which portions of the connecting portion bend like a hinge. Example hinges or straps with hinge features are described in U.S. Patent Publication No. 2011-0313519 A1, published Dec. 22, 2011 (U.S. patent application Ser. No. 13/017,189); U.S. Patent Publication No. 2011-0313524 A1, published Dec. 22, 2011 (U.S. patent application Ser. No. 13/092,359); U.S. Patent Publication No. 2011-0313525 A1, published Dec. 22, 2011 (U.S. patent application Ser. No. 13/111,599); and U.S. Patent Publication No. 2011-0313526 A1, published Dec. 22, 2011 (U.S. patent application Ser. No. 13/155,327), incorporated herein by reference in their entireties.

The connecting portions or bars 364 can extend lengthwise laterally (as in FIG. 1) or longitudinally (as in FIG. 2) between opposing paddles of the haptic along an axis either substantially parallel or substantially perpendicular to the longitudinal axis of the IOL through line A-A. Moreover, the connecting portions are in various embodiments integral to the haptic 300 at each of the lateral ends (as shown in FIG. 1) or at each of the end distal to the optic 200 (as shown in FIG. 2), and are preferably of the same flexible material as the haptic. However, the connecting portions 364 may also be of a different material than the haptic 300, for example, such that the connecting portions are substantially more flexible than the haptic. In at least one embodiment, the connecting portions 364 may be from 0.1 to 1.5 mm in length. Preferably, the connecting portion 364 has a square or circular cross-section, but other cross-sectional solid shapes are specifically contemplated. Accordingly, in various embodiments, the cross-section has a width and height that are substantially equal and may be smaller than the length of the connecting portion or bar 364. For example, the width of the cross-section perpendicular to the length of the connecting portion or bar 364 may be less than 1.5, 1.4, 1.3, 1.2, or 1.0 times the height of the cross-section or may be smaller and possible larger in some embodiments. Similarly, the width of the cross-section perpendicular to the length of the connecting portion or bar 364 may be less than 2.0, 1.5, 1.2, or 1.0 times the length of connecting portion or bar or may be smaller and possible larger in some embodiments.

On insertion into the eye, the optic 200 and haptics 300 may be vaulted posteriorly. This effect is facilitated by the stretching, and potentially thinning, bending, and/or rotation of the connecting portions in response to the increase in pressure exerted by the capsular bag on the distal ends of the haptics.

In at least one embodiment, the longitudinal length of the IOL (e.g., from distal end to distal end, wherein the distal end is distal with respect to the optic 200) may be between approximately 9.0-11.0 mm, with the diameter as measured from the tips of the lateral finger projections with respect to the optic being between approximately 11.5-12.0 mm. The haptics 300 are in various embodiments between 3.0-6.0 mm wide and 0.20-0.75 mm thick, while the optic 200 may be approximately 5.0 mm in diameter and 1.0 mm thick at its center.

In various embodiments the connecting portions or connecting bars 364 are thin and experience more thinning when stretched. Without stretching, for example, the connecting portions or connecting bars 364 may be thin with respect to the optic 200 and the lens 100. In certain embodiments, for example as shown in FIG. 2, the connecting portion or connecting bar 364 may have a width in the transverse direction (e.g., parallel to the x-axis) less than 50%, 40%, 30%, 20%, 10%, 5% or less of the width or diameter of the optic 20. Similarly, the connecting portions or connecting bars 364 may have a thickness orthogonal to the transverse and longitudinal directions (e.g., parallel to the z-axis) that is less than 50%, 40%, 30%, 20%, 10%, 5% or less of the diameter of the width or diameter of the optic 20. The width and thicknesses may be greater than 0.5% or 1% of width or diameter of the optic 20 in some embodiments.

The dimensions described above allow for adequate stretching. Additionally, such widths may reduce the incidence of tearing when inserting the IOL into the small opening made in the sclera or cornea of the eye. The IOL is rolled to facilitate insertion and the resultant twisting can introduce shear forces on wider connections, which may cause tearing. Having narrow widths reduces the shear force and permits twisting without tearing.

The connecting portions or bars 364 such as shown in FIGS. 1 and 2 being thin permit stretching. In various embodiments, the connecting portions or bars 364 stretch and thereby increase their length by at least 0.5, 1.0, 1.5, or 2.0 times of their length or more.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

The embodiments described in detail above are considered novel over the prior art of record and are considered critical to the operation of at least one aspect of the invention and to the achievement of the above-described objectives. The words used in this specification to describe the instant embodiments are to be understood not only in the sense of their commonly defined meanings, but to include by special definition in this specification: structure, material, or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and what incorporates the essential ideas.

The scope of this description is to be interpreted only in conjunction with the appended claims and it is made clear, here, that the named inventor believes that the claimed subject matter is what is intended to be patented.

The invention claimed is:

1. An intraocular lens having a longitudinal axis, the intraocular lens comprising:
   a lens optic,
   at least two longitudinally rigid haptics inseparably attached directly to said optic, each of said haptics having a proximal portion and a distal portion and extending distally from said optic,
   said optic being capable of vaulting posteriorly,
   each of said haptics comprising a laterally extending connecting bar located in its proximal portion, the connecting bar being configured to rotate about an axis substantially perpendicular to the longitudinal axis of the lens,
   each connecting bar being formed by a transverse slot in each haptic in cooperation with a part of each haptic located between each slot and said optic, which part of each haptic has a transverse dimension less than the transverse dimension of each slot.

2. The intraocular lens of claim 1, wherein said intraocular lens is uniplanar.

3. The intraocular lens of claim 1, wherein each of said haptics comprises a longitudinally rigid frame at least partially embedded in a flexible material.

4. The intraocular lens of claim 3, wherein each connecting bar comprises said flexible material.

5. The intraocular lens of claim 1, wherein each of the connecting bars has a cross-sectional shape perpendicular to its length which is circular, ovular or quadrilateral.

6. The intraocular lens of claim 1, wherein each of the connecting bars has a length between about 0.1 mm and 2.0 mm.

7. The intraocular lens of claim 1, wherein each of the connecting bars is configured to twist around an axis substantially perpendicular to the longitudinal axis of the lens upon an end-to-end compressive force from the capsular bag to position the optic posteriorly in the capsular bag upon implantation.

8. The intraocular lens of claim 1, wherein the optic and each haptic comprise the same material.

9. The intraocular lens of claim 8, wherein the optic comprises acrylic.

10. The intraocular lens of claim 1, wherein the optic comprises silicone.

11. The intraocular lens of claim 3, wherein the flexible material is silicone.

12. The intraocular lens of claim 3, wherein each frame comprises acrylic.

13. The intraocular lens of claim 3, wherein each frame comprises polyimide.

14. The intraocular lens of claim 1, wherein each haptic has projections or fingers extending from the distal portions of the haptics to engage the capsular bag.

15. The intraocular lens of claim 2, wherein the haptics are capable of vaulting posteriorly after insertion into the eye.

16. The intraocular lens of claim 1, wherein each connecting bar is flexible.

17. An intraocular lens having a longitudinal axis, the intraocular lens comprising:
   a lens optic,
   at least two substantially longitudinally rigid haptics inseparably attached directly to said optic, each haptic having a body extending distally from said optic and having a proximal portion and a distal portion,
   each of said haptics comprising a pair of opposing substantially rigid paddles, wherein each paddle extends laterally from the body of one of the haptics and toward a paddle of another one of the haptics such that an end portion of each paddle is a free end,
   each of said haptics having a transverse slot in its proximal portion, and
   each of said haptics comprising a laterally extending connecting bar adjacent to each slot,
   said connecting bars being formed by a part of each haptic between each slot and said optic in cooperation with each slot and being configured to rotate about an axis which is substantially perpendicular to the longitudinal axis of the lens.

18. The intraocular lens of claim 17, wherein each of said haptics comprises a longitudinally rigid frame at least partially embedded in a flexible material.

19. The intraocular lens of claim 18, wherein each frame extends into the end portion of each paddle.

20. The intraocular lens of claim 17, wherein said lens is uniplanar.

21. The intraocular lens of claim 20, wherein said lens is capable of vaulting posteriorly when implanted in an eye.

22. The intraocular lens of claim 17, wherein the optic and each haptic comprise the same material.

23. The intraocular lens of claim 22, wherein the optic comprises acrylic.

24. The intraocular lens of claim 18, wherein said flexible material is silicone.

25. The intraocular lens of claim 17, wherein each connecting bar comprises a flexible material.

26. The intraocular lens of claim 18, wherein each frame comprises acrylic.

27. The intraocular lens of claim 17, wherein each haptic has at least one projection or finger extending laterally from its distal portion.

\* \* \* \* \*